United States Patent [19]

Van Pool et al.

[11] Patent Number: 4,490,572
[45] Date of Patent: Dec. 25, 1984

[54] REMOVAL OF ORGANIC FLUORIDES FROM HF ALKYLATION PRODUCTS

[75] Inventors: Joe Van Pool; Paul D. Hann, both of Bartlesville, Okla.

[73] Assignee: Phillips Petroleum Company, Bartlesville, Okla.

[21] Appl. No.: 567,036

[22] Filed: Dec. 30, 1983

[51] Int. Cl.³ ............................ C07C 7/00; C07C 2/56
[52] U.S. Cl. ................................... 585/800; 585/712
[58] Field of Search ............................... 585/712, 800

[56] References Cited

U.S. PATENT DOCUMENTS

| 3,204,010 | 8/1965 | Van Pool | 585/712 |
| 3,204,011 | 8/1965 | Hettick et al. | 585/703 |
| 3,209,051 | 9/1965 | Bauer et al. | 585/331 |
| 3,253,054 | 5/1966 | Van Pool | 585/712 |
| 3,763,265 | 10/1973 | Hutson, Jr. et al. | 585/703 |
| 3,767,727 | 10/1973 | Chapman | 585/331 |
| 3,919,342 | 11/1975 | Chapman | 585/703 |
| 3,929,924 | 12/1975 | Chapman | 585/712 |
| 4,161,497 | 7/1979 | Makovec et al. | 585/714 |
| 4,182,924 | 1/1980 | Chapman | 585/712 |

*Primary Examiner*—Curtis R. Davis
*Attorney, Agent, or Firm*—A. W. Umphlett

[57] ABSTRACT

A method for removing organic fluorides from HF alkylation propane in which a stream of relatively pure liquid HF obtained by settling liquid HF from the liquefied hydrocarbon passed to the overhead accumulator common for both the depropanizing column and a hydrogen fluoride stripping column is intimately contacted with a stream of liquid hydrocarbon containing organic fluorides derived from condensing the mixed overhead vapor from a depropanizing column and overhead vapor from an HF stripping column in the process of separating products from a hydrogen fluoride alkylation. In preferred embodiments, the contacting takes place in the static mixer.

6 Claims, 3 Drawing Figures

4,490,572

REMOVAL OF ORGANIC FLUORIDES FROM HF ALKYLATION PRODUCTS

BACKGROUND OF THE INVENTION

This invention relates to the treatment of organic compounds with liquid hydrogen fluoride (HF). In one aspect, it relates to removal of organic fluorides from organic materials containing organic fluorides. In one specific aspect, it relates to an improved process for the removal of alkyl fluorides from a low-boiling hydrocarbon such as propane.

In processes where fluorine-containing catalysts such as hydrogen fluoride and boron-trifluoride are used, small proportions of organic fluorine-containing by-products are formed. These processes can involve such reactions as isomerization, polymerization, alkylation, and disproportionation of relatively low-boiling hydrocarbons.

In alkylation processes using an HF catalyzed reaction in which alkyl fluorides are formed, the removal of these fluoride contaminants from the propane produced by the alkylation using only conventional distillation steps is practically impossible. The presence of the alkyl fluorides in the product propane is objectionable for many of the end uses of the propane. For example, when organic fluoride is present in liquefied proprane to be used as LPG fuel, the combustion products contain HF which is produced by the combustion of the organic fluoride present in the propane. This produced HF will enter the atmosphere in the combustion gases as a hazardous contaminant of the environment. There have been many proposals of methods for the removal of organic fluorides from the by-product propane in a process such as HF catalyzed alkylation. Many of these processes are expensive but are quite adequate. It is, however, always of interest when a hitherto unknown process for the removal of alkyl fluorides from propane is brought forth, especially when the process requires relatively simple alteration to standard operating apparatus and process.

It is, therefore, an object of this invention to provide a method for removing alkyl fluorides from the propane by-product of HF alkylation. It is another object of this invention to provide a propane by-product of HF alkylation that is considerably reduced in alkyl fluoride content.

Other aspects, objects and various advantages of this invention will become apparent upon reading the specification, the claims and studying the drawing attached hereto.

SUMMARY OF THE INVENTION

According to this invention, a method is provided for removing organic fluorides from a propane stream recovered from an HF alkylation of an isoparaffin, e.g. isobutane, with an olefin, e.g. propylene and/or at least one of butene-1, butenes-2, and isobutylene. This method for removing organic fluorides from propane containing the same requires a minimum of additional equipment for the HF alkylation plant. This additional equipment, in our preferred operation, comprises a pump for liquid HF, a static mixer and interconnecting piping. Liquid HF recovered from the overhead of the depropanizer and from the hydrogen fluoride (HF)stripping column, which is relatively pure HF, is used to contact in a static mixer the liquid hydrocarbon condensate containing organic fluorides produced by condensing vapor from the depropanizer overhead and the HF stripping column overhead, and charging the liquid admixture to the alkylation unit's depropanizer overhead accumulator, thereby permitting recovery of propane liquid of decreased organic fluoride content.

In one embodiment of the invention, the stream containing organic fluorides is the liquefied mixed overhead containing propane, HF, isobutane, and organic fluorides from the depropanizing column and the hydrogen fluoride stripping column.

In another embodiment of the invention, the stream is the propane yield stream containing organic fluorides and is derived by settling HF from liquefied mixed overhead from the depropanizing column and the hydrogen fluoride stripping column.

The process of this invention can be best understood in conjunction with the drawing in which.

Figure 1:
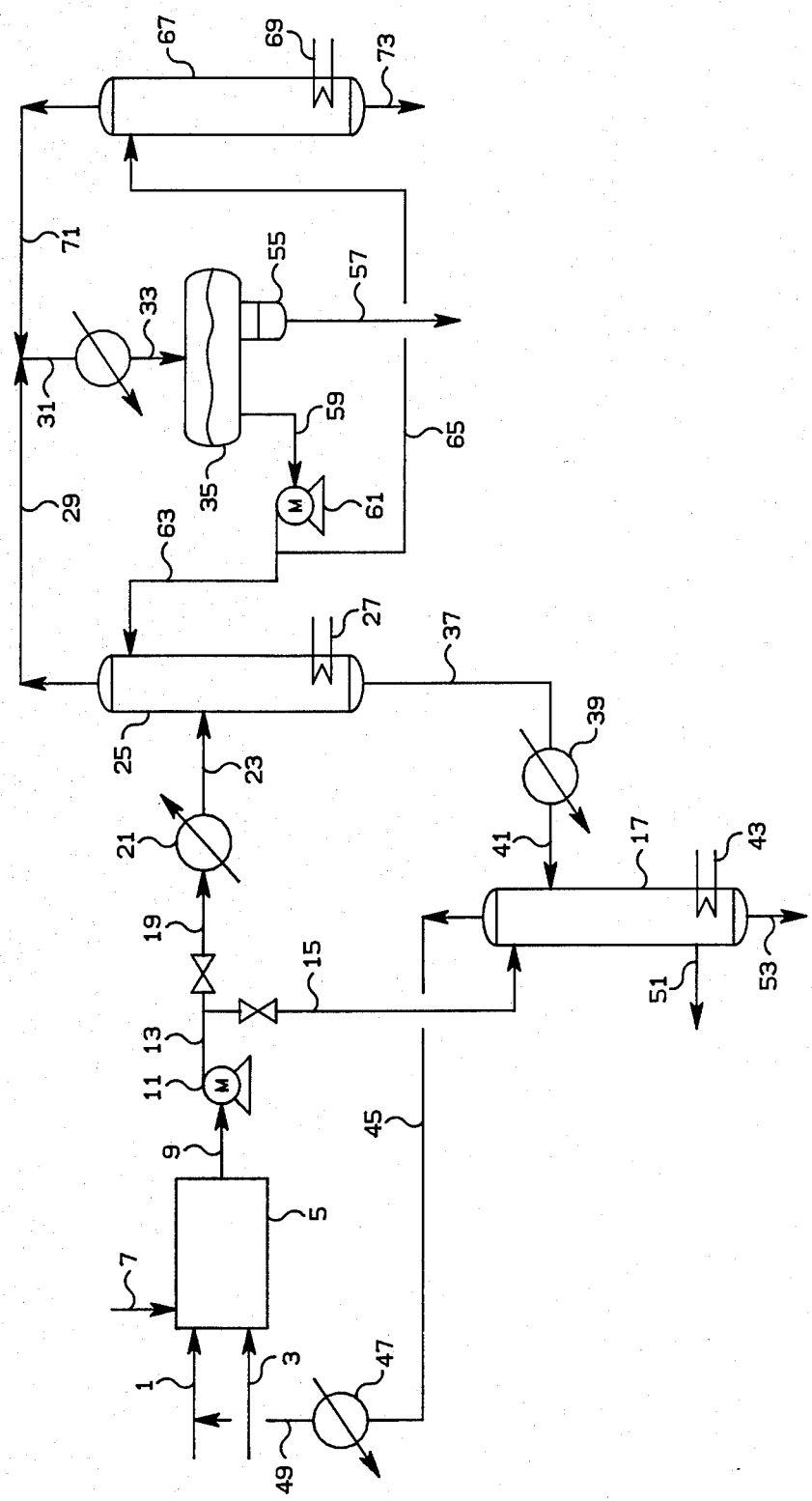
FIG. 1 is a schematic flow diagram illustrating a typical HF catalyzed alkylation process with recovery of products and by-products.

Referring now to FIG. 1, a suitable charge of feed stock such as isobutane through line 1 and propylene and/or at least one butylene through line 3 is passed into HF alkylation reactor-settler 5 along with hydrogen fluoride catalyst through line 7 at reaction conditions to produce a hydrocarbon alkylate product, containing organic fluorides and dissolved HF, which is passed by line 9 and pump 11 through line 13 to be split into two feed streams which pass in part through line 15 to isostripper 17 and, in part, through line 19, heater 21 and line 23 to depropanizing column 25.

Stream 23 contains sufficient propane to yield propane product. In some operations, isostrippper 17 and depropanizer 25 are combined into a single tower (not shown). The depropanizing column 25 is indirectly heated by heat exchange fluid in kettle coil 27 and produces an overhead, vaporized stream, that contains propane, some isobutane, HF, and alkyl fluoride contaminants, which is passed through line 29, condenser 31 and line 33 into overhead accumulator 35. The kettle liquid from depropanizing column 25 contains some propane, isobutane, and heavier material which is passed through line 37, heat exchanger 39 and line 41 as part of the feed processed by isostripping column 17.

The isostripping column which is indirectly heated by heat exchange fluid in kettle coil 43 produces an overhead vapor containing isobutane which is recycled through line 45, condenser 47, and line 49 as diluent isobutane recycle into the alkylation reactor 5. A side stream of vaporous normal butane present in the alkylation system is removed from the isostripping column 17 by line 51, and a product stream of liquid alkylate, which contains isopentane and heavier material, is recovered through line 53.

The condensed overhead from the depropanizing column collected in accumulator 35 is allowed to phase separate so that liquid HF collects in the settling leg 55 and is removed through line 57, usually for recycle the reactor. The upper liquid hydrocarbon phase from the accumulator with the HF removed (but containing soluble HF) passes through line 59 and pump 61 as part of the material returned to depropanizing column 25 by line 63 as reflux, and the rest of the material (containing the yield propane) passes through line 65 as feed for the HF stripping column 67.

In the HF stripping column 67, which is indirectly heated by a heat exchange fluid in heating coil 69, an overhead vapor stream containing HF and propane is produced which is returned through line 71, condenser 31 and line 33 to the accumulator 35. Yield propane containing excessive organic fluoride is removed through line 73.

In the processes described above, alkyl fluoride contaminant, mainly isopropyl fluoride that finds its way into the HF stripping column becomes a problem in the yield propane. According to the present invention, as will be described below in conjunction with FIG. 2 and FIG. 3, the process streams at the overhead accumulator 35 (which is also a phase separator) are manipulated to provide the required reduction in the amount of alkyl fluoride that finds its way into the yield propane. This process utilizes simple alteration and addition to the standard operating equipment.

Figure 2:
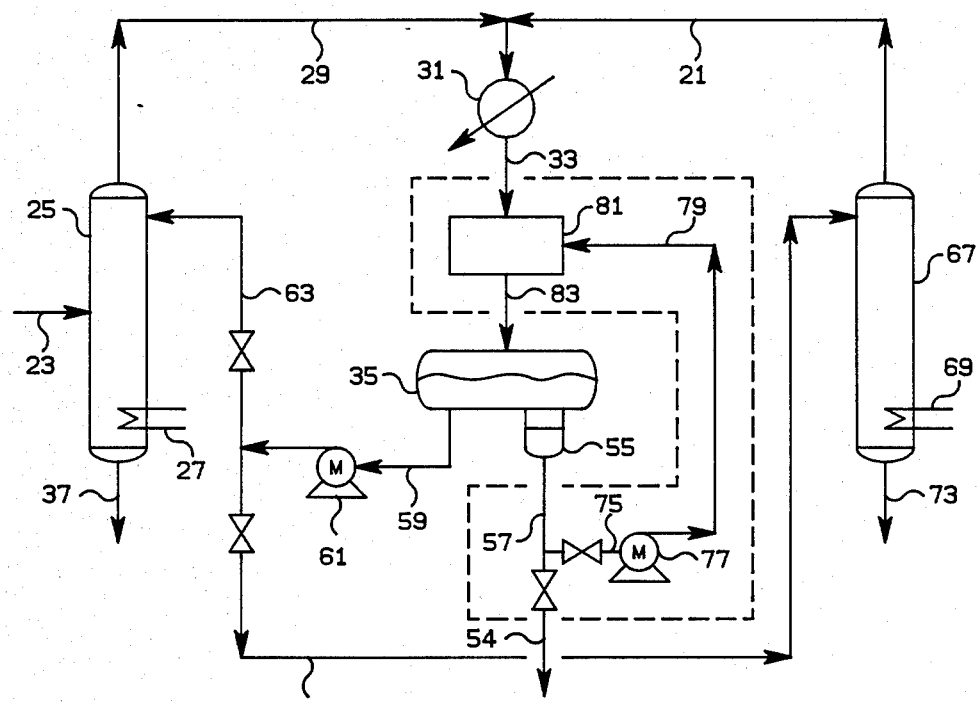
FIG. 2 is a schematic flow diagram illustrating a now preferred specific embodiment of the present invention for contacting the liquefied mixed overhead from the depropanizing column and a hydrogen fluoride stripping column with relatively pure HF obtained by settling HF from the liquefied overhead accumulator.
Figure 3:
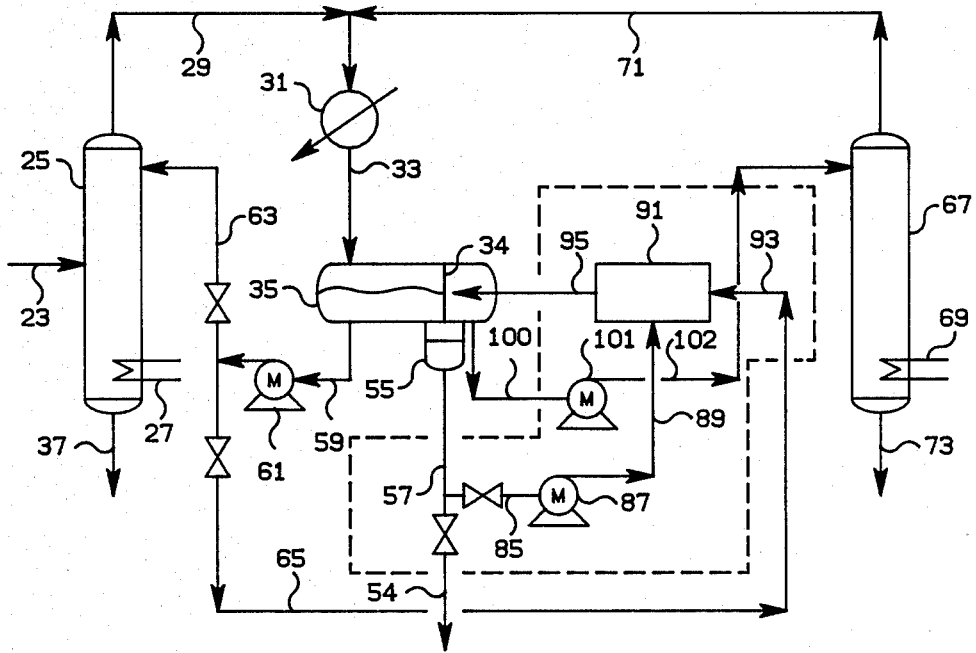
FIG. 3 is a schematic flow diagram illustrating another specific embodiment of the invention in which a stream (the propane yield portion) derived by settling HF from the liquefied mixed overhead from the depropanizing column and the hydrogen fluoride stripping column is contacted with the relatively pure liquid HF settled from the overhead accumulator.

In FIG. 2 and FIG. 3, like numbers will be used from FIG. 1 where the same equipment is described. The apparatus for use in the improvements of the process is set out in FIG. 2 and in FIG. 3 by a dashed outline.

Referring now to FIG. 2, the preferred embodiment of this invention, there is illustrated the process wherein relatively pure HF that is collected in settling leg 55 is, in part, passed through line 75, pump 77 and line 79 into an intimate contacting device which can be any device in which sufficient intimate contact can be obtained to react in the presence of HF, the alkyl fluoride contaminant and isobutane present in the overhead streams condensed in condenser 31 and passed by line 33 into this intimate contact with the HF. Here a static mixer is illustrated as the intimate contacting device 81. The intimate contact of the relatively pure HF and the stream containing the contaminant alkyl fluoride substantially reduces the amount of alkyl fluoride that remains in the hydrocarbon passed by line 83 into accumulator 35, and, thereby, the liquid hydrocarbon removed through line 59, pump 61 and line 65 into the HF stripping column 67 is substantially reduced in alkyl fluoride content, as desired. This embodiment of FIG. 2 requires only minimum additional equipment; pump 77, static mixer 81, and connecting conduit means.

Similarly, as shown in the embodiment of FIG. 3, the HF from settling leg 55 is, in part, diverted from line 57 through line 85, pump 87 and line 89 into a static mixer 91 where it is intimately contacted with the hydrocarbon liquid contaminated with organic fluoride, from which all but soluble HF has been removed, which has been passed through line 59, pump 61, line 65 and line 93 into the static mixer 91. The admixing of the relatively pure HF and the hydrocarbon liquid containing the alkyl fluoride contaminant substantially reduces the amount of contaminant so that the liquid passing through line 95 back into the accumulator 35 is substantially reduced in contaminant. Baffle 34 divides accumulator 35 into two hydrocarbon sections. The mass of hydrocarbon-HF in conduit 95 enters accumulator 35 on, as shown, the right hand section of accumulator 35 so that phase separation occurs. The HF liquid phase enters leg 55. The cleaned or organic fluoride-lean hydrocarbon liquid phase passes from accumulator 55 via line 100, pump 101, and line 102 and is charged to column 67.

Set out below is a calculated example showing the operation of the present invention with the now preferred improvement operation as illustrated in FIG. 2 incorporated into the overall operation of the system set out in FIG. 1. This example incorporates the use of a KOCH static mixer manufactured by KOCH Engineering Co., Inc., 411 East 37th Street, N. Wichita, Kans. The example sets out the operating conditions for the major pieces of equipment and the flows at the major points in the system which will show the overall operation of the system.

EXAMPLE

| Calculated Operation | | |
|---|---|---|
| Operations: | | |
| Depropanizer (25) | | |
| Pressure, psia | | 315 |
| Top Temp., °F. | | 129 |
| Bottom Temp., °F. | | 214 |
| Accumulator (35): | | |
| Pressure, psia | | 280 |
| Temperature, °F. | | 85 |
| Static Mixer (81,91) | | |
| Pressure, psia | | 282 |
| Temperature, °F. | | 85 |
| Stripper (67): | | |
| Pressure, psia | | 315 |
| Top Temp., °F. | | 129 |
| Bottom Temp., °F. | | 149 |
| Isostripper (17): | | |
| Pressure, psia | | 120 |
| Top Temp., °F. | | 131 |
| Bottom Temp., °F. | | 328 |
| Flows: | | |
| (13) Hydrocarbon from HF Reactor Settler, B/D | | 72;720 |
| (15) To Isostripper, B/D | | 57,600 |
| (23) To Depropanizer, B/D | | 15,120 |
| (53) Alkylate Yield, B/D | | 6,000 |
| (37) Depropanizer Bottoms, B/D | | 13,680 |
| HF, ppm by wt. | 10 | |
| Organic Fluorides, ppm by wt. | 200 | |
| (45) Recycle/Isobutane, B/D | | 64,920 |
| (29) Depropanizer Overhead, B/D (as liquid) | | 14,880 |
| Component | Vol. % | |
| Propane | 98 | |
| Isobutane | 2 | |
| Normal Butane | 0 | |
| Total | 100 | |
| HF, ppm by wt | 26,800 | |
| Organic Fluorides, ppm by wt. | 100 | |
| (71) Stripper Overhead, B/D (as liquid) | | 720 |
| Component | Vol. % | |
| Propane | 98 | |
| Isobutane | 2 | |
| Normal Butane | 0 | |
| Total | 100 | |
| HF, ppm by wt. | 16,200 | |
| Organic Fluorides, ppm by wt. | 100 | |
| (79) HF to KOCH mixer, B/D | | 12,000 |
| (54) HF to Reactor, B/D | | 420 |
| (73) Propane Yield, B/D | | 1,440 |
| Organic Fluorides, ppm by wt. | 30 | |

We claim:

1. A method for removing organic fluorides from HF catalyzed alkylation propane comprising:
   (a) intimately contacting
      (1) a stream of liquid HF obtained by settling liquid HF from the overhead accumulator common for both a depropanizing column and a hydrogen fluoride stripping column, with
      (2) a liquid hydrocarbon stream containing organic fluorides derived from the condensing mixed vapor overhead from a depropanizing column and from a hydrogen fluoride stripping column in the process of separating products from a hydrogen fluoride alkylation, and
   (b) passing the liquid admixture stream obtained from said contacting into said accumulator.

2. A method of claim 1 wherein the liquid hydrocarbon stream containing organic fluoride is recovered from the liquefied mixed overhead from the depropanizing column and an HF stripping column.

3. A method of claim 1 wherein the liquid hydrocarbon stream containing organic fluoride is a stream derived by settling HF from the liquefied mixed overhead from the depropanizing column and the HF stripping column.

4. A method of claim 1 wherein said contacting takes place in a static mixer.

5. A method of claim 2 wherein said contacting takes place in the static mixer.

6. A method of claim 3 wherein said contacting takes place in a static mixer.

* * * * *